United States Patent [19]
Osawa et al.

[11] Patent Number: 5,557,402
[45] Date of Patent: Sep. 17, 1996

[54] SURFACE FLAW DETECTING APPARATUS OF WORKPIECE

[75] Inventors: Toshihiro Osawa, Ikoma; Shizuki Sasakura, Yao; Haruhiko Terauchi, Osaka, all of Japan

[73] Assignee: Koyo Machine Industries Co., Ltd., Yao, Japan

[21] Appl. No.: 425,497

[22] Filed: Apr. 20, 1995

[30] Foreign Application Priority Data

Sep. 30, 1994 [JP] Japan .................................. 6-261704

[51] Int. Cl.6 ................................................ G01N 21/48
[52] U.S. Cl. ........................................ 356/237; 356/426
[58] Field of Search ................................... 356/237, 239, 356/240, 73, 426–428, 429–431, 445–446; 209/523, 524, 526, 577–579, 587, 599, 938; 250/559.42, 559.45

[56] References Cited

U.S. PATENT DOCUMENTS 3,651,937  3/1972  Kronseder ............................ 209/526
3,832,065  8/1974  Sullivan et al. ..................... 356/237
3,974,540  8/1986  Bonner ................................. 15/339
5,277,320  1/1994  Corkill et al. ....................... 356/237

Primary Examiner—Hoa Q. Pham
Attorney, Agent, or Firm—Nikaido, Marmelstein, Murray & Oram LLP

[57] ABSTRACT

A surface flaw detecting apparatus of workpiece fast in flaw detecting speed, significantly shortened in the line cycle time, and simple and inexpensive in structure. By means of a control device, while a work rotating device is rotating a work about its axial line, a cleaning device remove soiling from the surface of the work, and its surface is illuminated by a lighting device, and its reflected light is detected by a line sensor camera, and presence or absence of flaw on the work surface is judged by a judging device from the result of detection. This series of measuring operation is done while the work makes a full revolution about its axial line, and hence as compared with other optical measurement, the measuring time may be shortened remarkably.

15 Claims, 9 Drawing Sheets

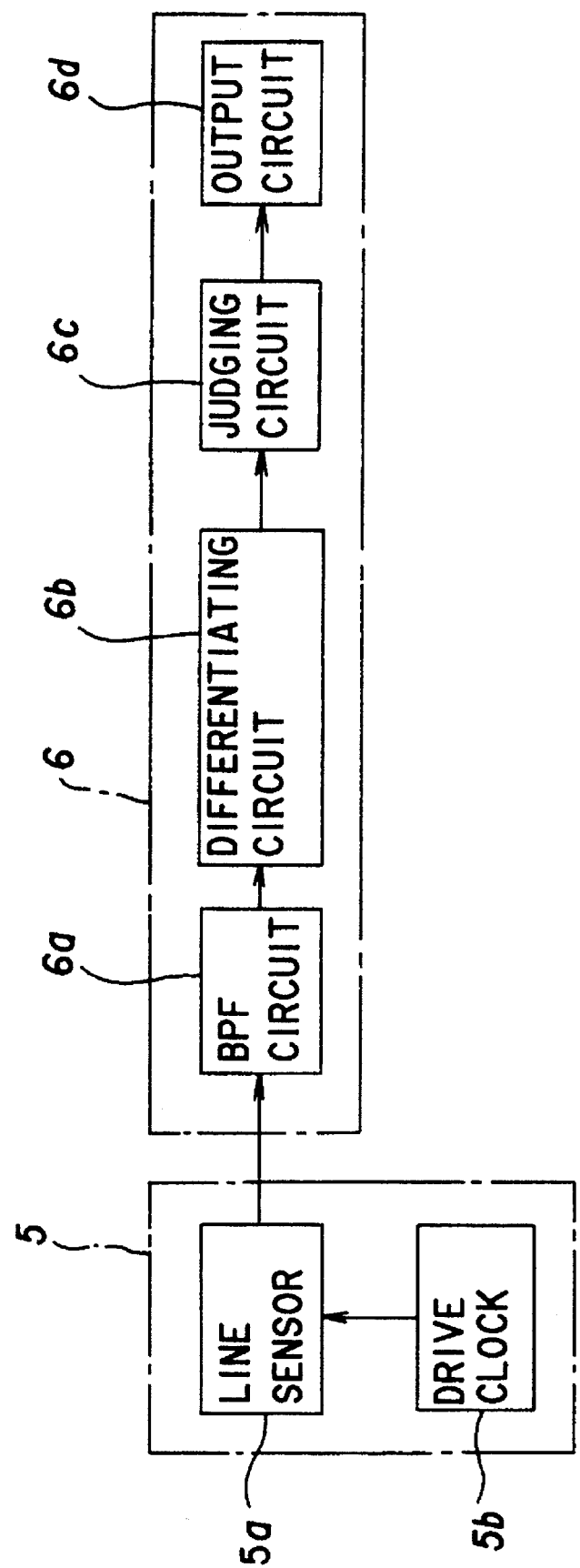

SURFACE FLAW DETECTING APPARATUS OF WORKPIECE

BACKGROUND OF THE INVENTION

1. Field of the Invention

The present invention relates to a surface flaw detecting apparatus of workpiece, and more particularly to a surface flaw detecting apparatus of workpiece disposed, for example, at an exit side of a machine tool for optically detecting or measuring the presence or absence of flaw on the surface of the workpiece while rotating the bar-shaped workpiece after being processed about its axial line.

2. Description of the Related Art

As this type of optical surface flaw detecting apparatus, one comprising a laser sensor composed of a laser oscillator and a photo detector is known. In flaw detecting operation of this surface flaw detecting apparatus, for example as shown in FIG. 10 (a), while rotating a bar-shaped workpiece (hereinafter called work) (W) about its axial line (about 3,000 rpm), and moving a laser sensor (a) gradually in the axial direction of the work (W) (about 25 µm/revolution), the work surface is spirally scanned by the laser sensor (a).

When the axial length of the work W is relatively long, in order to shorten the measuring time, as shown in FIG. 10 (b), a plurality of laser sensors (a) are disposed parallel (three in this example), corresponding to the work length, and they are simultaneously put in action to scan the work surface.

To prevent error in measurement by the laser sensor (a), prior to the measurement, a step to clean the surface of the work (W) is needed. In this type of surface detecting apparatus, for this purpose, an apparatus for a wiping step independent of the measuring step is provided.

In such laser sensor system, however, because of the spiral scanning method as mentioned above, the flaw detecting speed is limited, and if the preceding step of machining is done at high speed, the measuring time per work (W) may become even longer than the machining time. Accordingly, the series of processing steps of the works (W) is stagnant, which may result in increase of line cycle time (machining time+wiping time+measuring time).

For example, when measuring a work (W) of 20 mm in diameter and 300 mm in length by using three laser sensors (a), (a), (a) as shown in FIG. 10 (b), the measuring time takes about 60 seconds. Besides, wiping of the work surface requires another step, and hence the total cycle time is about 80 seconds.

Even in optical measuring method, rotary motion of the work (W) and moving motion of the laser sensor (a) in the work axial direction are mechanical. Accordingly, relating with the spot measurement of the laser sensor (a), a relative deflection is likely to occur between the work (W) and the laser sensor (a), thereby producing a measuring error, and high reliability is not obtained in the measuring precision. In particular, when the rotating speed of the work (W) is increased in order to shorten the measuring time, vibration due to deflection of the work (W) becomes larger, and more measuring errors tend to occur.

SUMMARY OF THE INVENTION

It is hence a primary object of the invention to present a novel surface flaw detecting apparatus of workpiece solving the above problems.

It is other object of the invention to present a surface flaw detecting apparatus of workpiece being fast in flaw detecting speed so as to be capable of shortening the line cycle time significantly.

It is another object of the invention to present a surface flaw detecting apparatus of workpiece of which mechanical motion during flaw detection and measurement is rotation of works only, having almost no relative deflection between the works and an optical sensor, thereby obtaining measurement of high reliability and high precision.

It is a different object of the invention to present a surface flaw detecting apparatus of workpiece in which the work surface cleaning step is done prior to and almost simultaneously with work flaw detecting operation, so as to be practically free from effects on the line cycle time.

It is a further different object of the invention to present a surface flaw detecting apparatus of workpiece which is short in time required for work loading, so that the line cycle time may be further shortened.

It is a still different object of the invention to present a surface flaw detecting apparatus of workpiece which is small in the number of mechanical moving parts, simple and compact in the entire constitution, few in troubles and low in product cost.

A surface flaw detecting apparatus of the invention comprises a work rotating device for rotating a work about an axial line, a cleaning device for removing soiling from the work surface, a lighting device for lighting the work surface, a line sensor for detecting the reflected light from the work surface, a judging device for judging presence or absence of flaw on the work surface from the sensor detecting result, and a control device for controlling the drive of these constituent devices by synchronizing mutually.

By the control device, while the work rotating device is rotating the work about its axial line, the cleaning device removes soiling from the work surface and the lighting device lights the surface, and the reflected light is detected by the sensor, and from the result of this detection, the judging device judges presence or absence of flaw on the work surface. The series of actions for measurement is completed while the work nearly makes a full revolution about the axial line, so that the measuring time is short.

These and other objects and features of the invention will be better appreciated and understood from the novel facts indicated in the following detailed description accompanied by the drawings and the claims.

BRIEF DESCRIPTION OF THE DRAWINGS

FIG. 9 is a block diagram showing an electric processing system in the surface flaw detecting apparatus.

DETAILED DESCRIPTION OF THE PREFERRED EMBODIMENT

Figure 1:
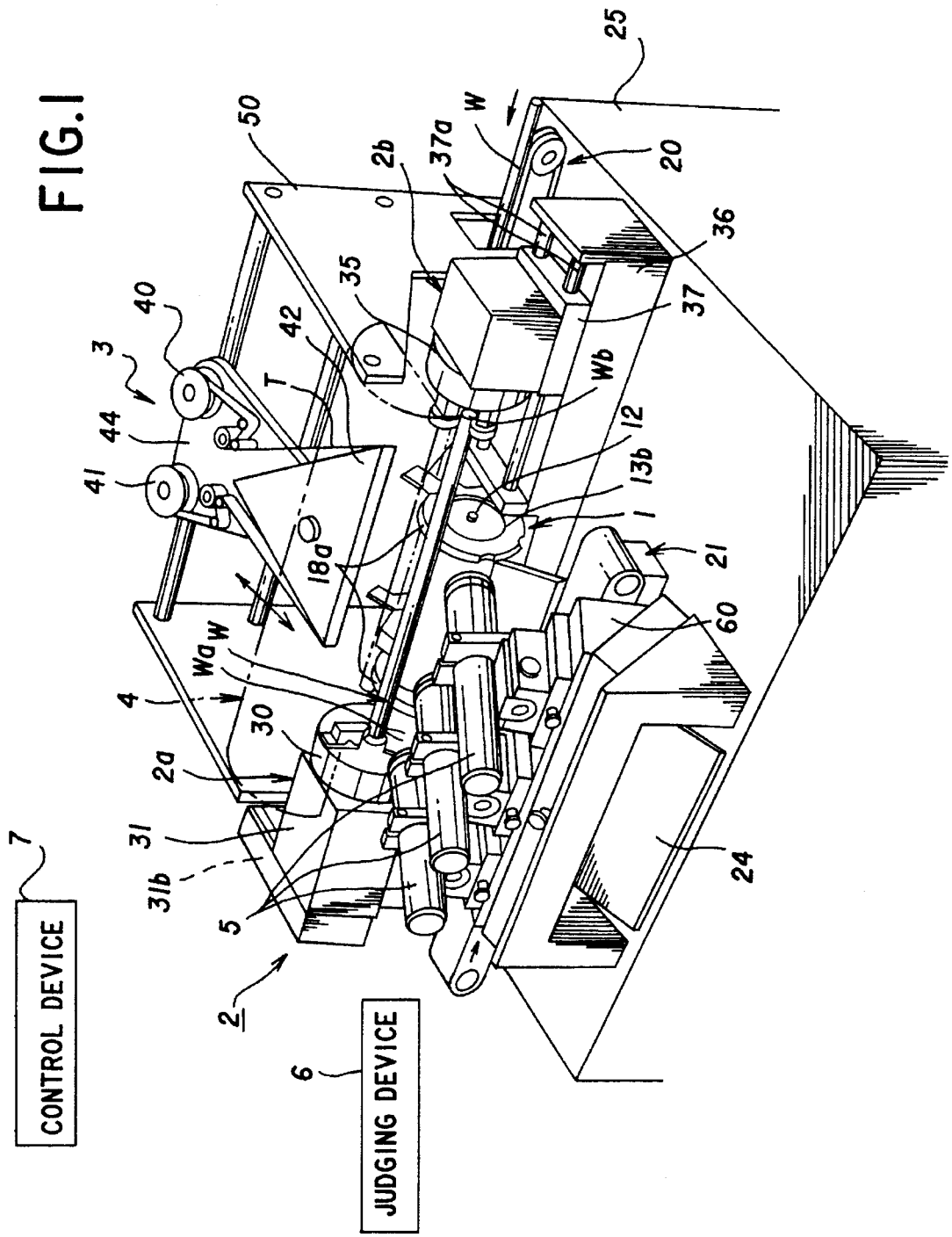
FIG. 1 is a perspective view showing a surface flaw detecting apparatus of workpiece according to an embodiment of the invention.

Referring now to the drawings, an embodiment of the invention is described in detail below.

FIG. 1 through FIG. 9 illustrate a surface flaw detecting apparatus of workpiece conforming to the invention, and same reference numerals refer to same constituent members or elements throughout the drawings.

This surface flaw detecting apparatus is specifically intended to detect and measure optically presence or absence of flaw on the surface of a bar-shaped work W. The surface flaw detecting apparatus mainly comprises a loader device 1 as loader means, a work rotating device 2 as work rotating means, a cleaning device 3 as cleaning means, a lighting device 4 as lighting means, a line sensor camera 5 as sensor means, a judging device 6 as judging means, and a control device 7 as control means. These constituent devices are individually described below.

A. Loader device 1

Figure 2:
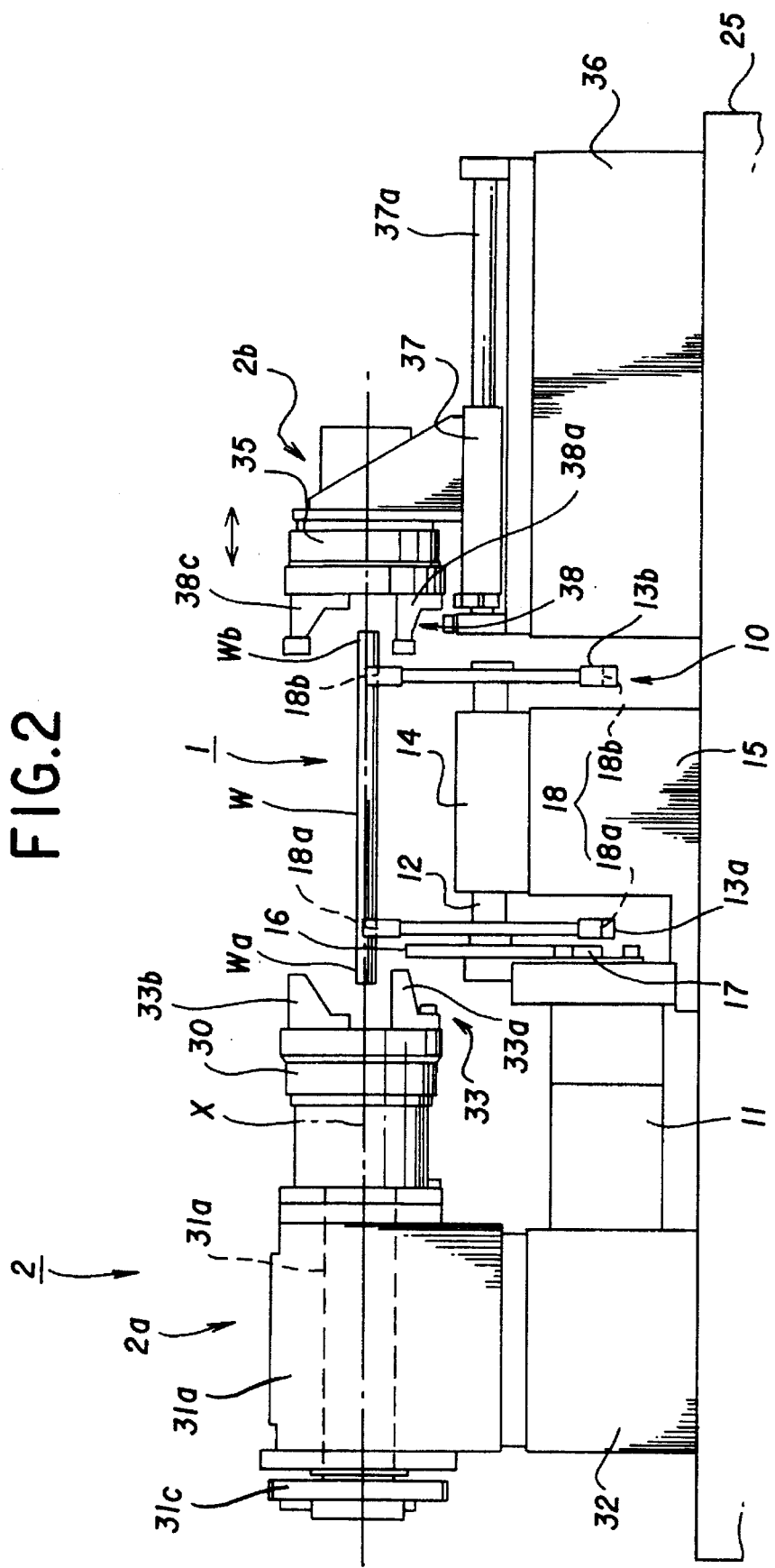
FIG. 2 is a side view showing the same surface flaw detecting apparatus.

The loader device 1 is intended to load and unload the work W on the work rotating device 2. The loader device 1 is, structurally as shown in FIG. 2, a rotary type loader device comprising a loader main body 10 and a rotary drive unit 11. The loader device 1 is disposed between the first and second chuck devices 2a, 2b in the work rotating device 2.

The loader main body 10 is constituted by mounting a pair of index plates 13a, 13b on both ends of a rotary support shaft 12. The rotary support shaft 12 is rotatably supported on a base 15 by means of a bearing 14, and its axial line is arranged to be parallel to the work rotation axial line X of the both chuck devices 2a, 2b. At one end of the rotary support shaft 12, a transmission gear 16 is installed and fixed. On the other hand, a drive gear 17 is attached and fixed to the drive shaft of the drive motor which is the rotary drive unit 11. These gears 16, 17 are mutually engaged and coupled. As the drive motor 11, an electric motor such as stepping motor may be preferably used. As described later, by driving rotation of the drive motor 11, the loader main body 10 is intermittently rotated in indices through the gears 17, 16.

The pair of index plates 13a, 13b are provided on the rotary support shaft 12. These index plates are disposed, confronting each other, at a specific interval and at right angle to the axial line of the rotary support shaft 12. On the outer peripheral parts of the both index plates 13a, 13b, work stores 18 for storing and supporting works W are disposed in plural positions at equal intervals in the peripheral direction.

Each work store 18 is composed of a pair of pockets 18a, 18b, and these pockets are formed in a confronting manner on the index plates 13a, 13b. The both pockets 18a, 18b are in the shape of being opened to the outer periphery of the index plates 13a, 13b, and both ends of the work W are put and supported in both pockets 18a, 18b. In the state of the work W being supported on the pockets 18a, 18b, the axial line of the work W is designed to be parallel to the work rotation axial line X of the chuck devices 2a, 2b. In the illustrated embodiment, the pockets 18a, 18b are in a semicircular shape corresponding to the circular section of the work W, but may be also formed in V-shape or other notch shape.

Figure 3:
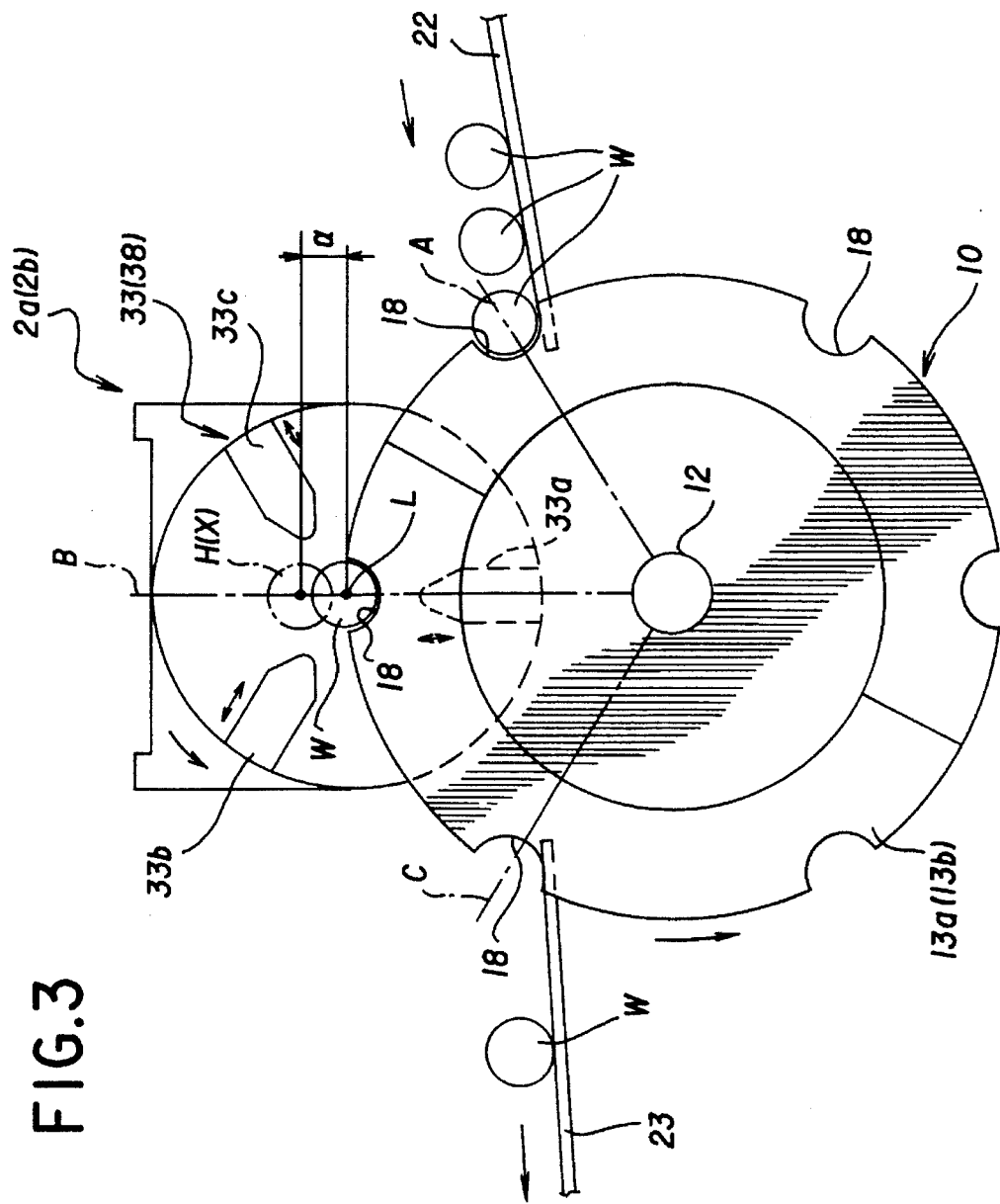
FIG. 3 is a side view showing a loader device and work rotating device of the surface flaw detecting apparatus.

The configuration of the work stores 18 (18a, 18b) is shown in FIG. 3. That is, in the state of one of the work stores 18, 18, . . . being indexed in work chuck position B, it is constituted so that the other two may be indexed in work entry position A and work exit position C. In the illustrated embodiment, six work stores 18 are disposed at equal intervals in the peripheral direction. As a result, three adjacent work stores 18, 18, 18 are disposed so as to correspond respectively to the index positions A, B, C. The configuration of the work stores 18 is not limited to the illustrated example alone, but is variable depending on the outside diameter of the index plates 13a, 13b, and location of the index positions A, B, C.

At the work entry position A, work chuck position B, and work exit position C, an inlet conveyor 20, chuck devices 2a, 2b of the work rotating device 2, and an outlet conveyor 21 are respectively disposed, in correspondence to the arrangement of the work stores 18, 18, . . . of the loader main body 10.

Both inlet conveyor 20 and outlet conveyor 21 are formed as belt conveyors extending parallel to the loader device 1. Between the inlet conveyor 20 and work entry position A, and work exit position C and outlet conveyor 21, an inlet chute 22 and an outlet chute 23 as shown in FIG. 3 are disposed in a slope state respectively. Therefore, exchange of works W on the work stores 18 of the loader 1 is achieved as the work W itself rolls and drops on the chutes 22, 23 by its own weight. At a side position of the exit conveyor 21, a rejection port 24 is provided in which defective works W are discharged.

The index rotating locus of the work stores 18, 18, that is, the locus of the work stores 18, 18, . . . passing while the loader main body 10 makes an index rotation is defined so as not to interfere mutually with the chuck devices 2a, 2b. This point is described later.

Thus, when the loader main body 10 makes an index rotation (arrow direction) by the drive motor 11, the following three actions are synchronized to take place parallel and simultaneously. i) The work W conveyed on the inlet conveyor 20 is put into the work store 18 at the work entry position A through the inlet chute. ii) The work W supported by the work store 18 at the work chuck position B is chucked by the chuck devices 2a, 2b of the work rotating device 2, that is, is loaded into the work rotating device 2. iii) The work W supported by the work store 18 at the work exit position C is discharged into the outlet conveyor 21 through the outlet chute 23.

B. Work rotating device 2

The work rotating device 2 is intended to rotate the work W about its axial line X. The work rotating device 2 specifically comprises the first and second chuck devices 2a, 2b mounted on an apparatus main body 25.

The first chuck device 2a comprises, as shown in FIG. 2, a drive chuck unit 30 for chucking one end Wa of the work W, and a drive unit 31 for driving and rotating the drive chuck unit 30. The first chuck device 2a is fixed on the apparatus main body 25 through a base 32.

Figure 4A:
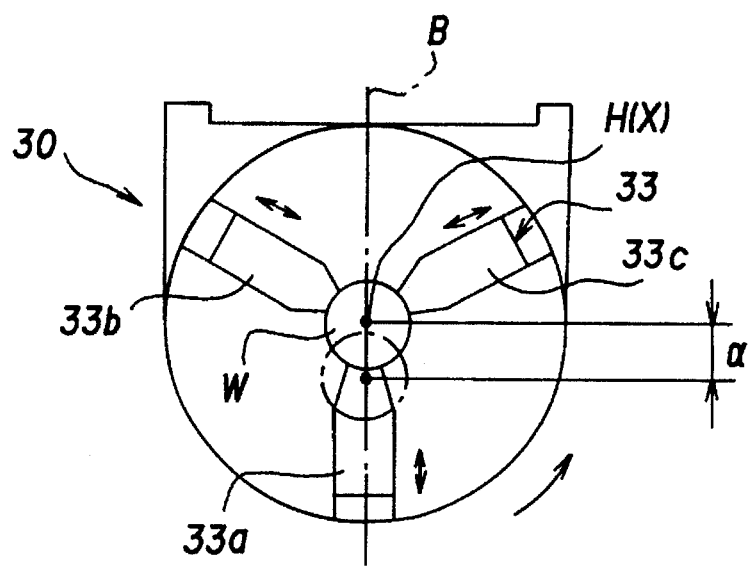
FIG. 4 is a front view showing a chuck device of the loader device, showing a first chuck device in FIG. 4 (a) and a second chuck device in FIG. 4 (b)
Figure 4B:
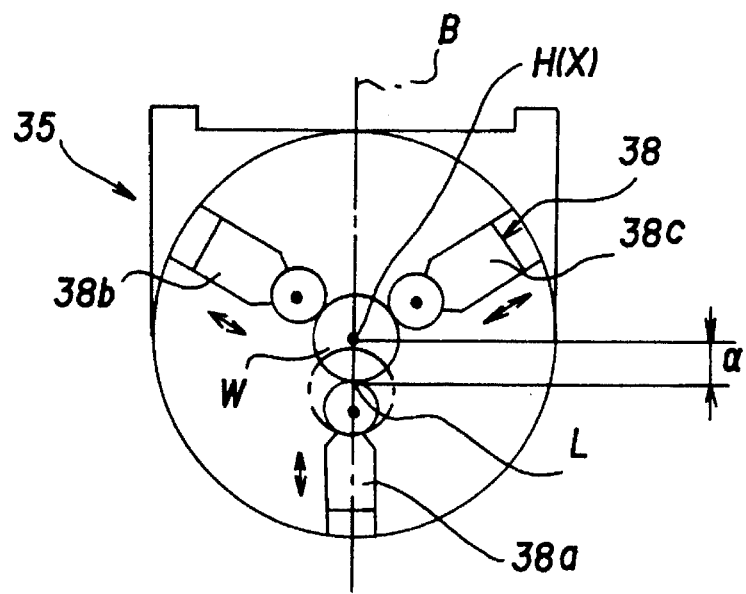

The drive chuck unit 30 is fitted to the front end of a rotary main shaft 31a of the drive unit 31. The drive chuck unit 30 has three pawls as shown in FIG. 4 (a), and three pawls 33 (33a, 33b, 33c) are designed to move back and forth in the radial direction (so as to open and close). These chuck pawls 33 are opened and closed by a drive source not shown in the drawing, and firmly clamp one end Wa of the work W in the closed state.

The drive unit 31 comprises the rotary main shaft 31a and a drive motor 31b for driving and rotating it, and the both are driven and coupled through a gear mechanism 31c. As the drive motor 31b, an electric motor such as AC servo motor may be used preferably.

The second chuck device 2b is fixed on the apparatus main body 25 through a base 36. The second chuck device 2b has a follower chuck unit 35, and this follower chuck unit 35 rotatably chucks and supports the other end Wb of the work W.

The follower chuck unit 35 is mounted on a chuck slide 37 provided on the base 26. The follower chuck unit 35 has three pawls as shown in FIG. 4 (b), and the three chuck pawls 38 (38a, 38b, 38c) having rotary rollers are designed to move back and forth in the radial direction (so as to open and close). These chuck pawls 38 are opened and closed by a drive source not shown in the drawing, and rotatably clamp the other end Wb of the work w in the closed state.

The chuck slide 37 is movable reciprocally on guide rods 37a, 37b in the direction of work rotary axial line X by means of a built-in drive source (not shown). By this move of the chuck slide 37, the interval between the drive chuck unit 30 and follower chuck unit 35 is adjustable depending on the length of the work W.

Consequently, at the work chuck position B, the work W is loaded into the work rotating device 2 from the rotary loader device 1, and the both ends Wa, Wb are chucked and supported by the drive chuck unit 30 and follower chuck unit 35. The drive chuck unit 30 is driven and rotated by the drive unit 31, and the work W is rotated only by specific angle in the arrow direction. The angle of rotation at this time is described later.

As mentioned above, meanwhile, it is constituted so that the both chuck units 30, 35 and the work stores 18, 18, ... of the rotary loader device 1 may not interfere with each other in this series of actions.

That is, as shown in FIG. 3, in the open state of the chuck pawls 33, 38 of the both chuck units 30, 35, the index rotary locus of the work stores 18, more specifically, the rotary locus of the works W held in the work stores 18 is defined so that the works W may pass through the chuck pawls without contacting them.

In the closed state of both chuck pawls 33, 38, from the clamped by these chuck pawls, the outer peripheral edges of the index plates 13a, 13b of the rotary loader device 1 is spaced. Accordingly, the work W and outer peripheral edges of the index plates 13a, 13b are defined so as not to contact with each other.

In other words, in the work chuck position B, the relation of the height position between the axial center (work center) L of the work W held in the work store 18, and the axial center (chuck center) H of the work W clamped in the chuck pawls is set so that the chuck center H may be slightly higher as shown in the diagram. As a result, when the work W held in the work store 18 is chucked and clamped by the chuck pawls 33, 38, the work W is slightly lifted from the work store 18 (in particularly, by the lifting action of the lower side chuck pawls 33a, 38a).

Therefore, in the moving range of the both chucks units 30, 35, whether in open state or in closed state, the work W will not contact with the chuck pawls 33, 38 or index plates 13a, 13b, so that the work W may not be damaged.

C. Cleaning device 3

Figure 5:
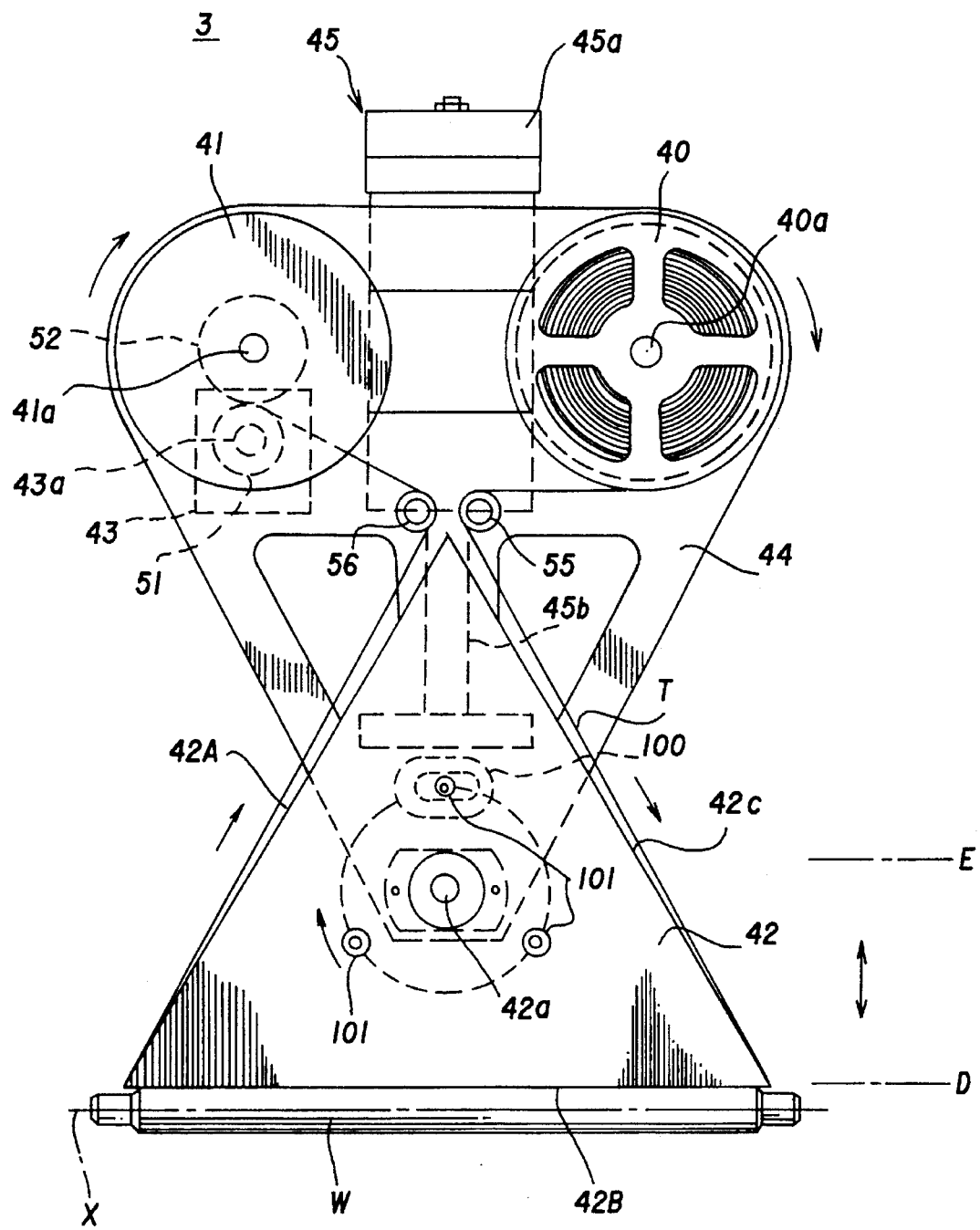
FIG. 5 is a plan view showing a cleaning device in the surface flaw detecting apparatus.
Figure 6:
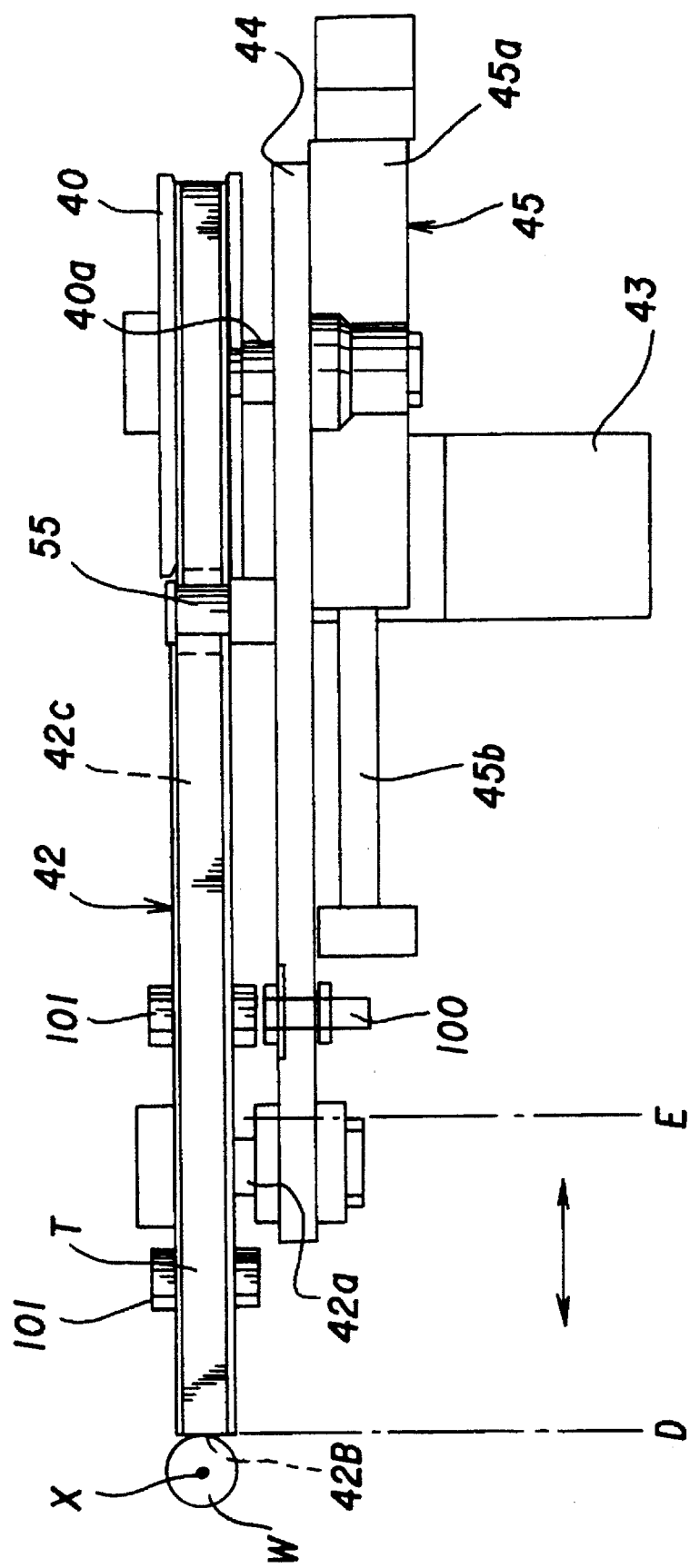
FIG. 6 is a side view of the cleaning device.

The cleaning device 3 is to wipe and remove soiling from the surface of the work W rotated by the work rotating device 2. The cleaning device 3 mainly comprises, as shown in FIGS. 5 and 6, a let-off reel 40 on which a cleaning cloth T is wound, a take-up reel 41, a cloth guide 42, and a rotary drive unit 43. These constituent components are mounted on a slide main body 44, and a reciprocal drive unit 45 for reciprocating the slide main body 44 is also provided.

The slide main body 44 has a nearly triangular shape in plan view as shown in FIG. 5, and is mounted on a stand 50 attached to the apparatus main body 25. On each peak of the slide main body 44, the let-off reel 40, take-up reel 41 and cloth guide 42 are rotatably supported by means of support shafts 40a, 41a, 42a, respectively.

The slide main body 44 is movable reciprocally (back and forth) in the arrow direction, relative to the work W chucked and held in the work rotating device 2, and is driven and coupled by the reciprocal drive unit 45. The reciprocal drive unit 45 comprises a reciprocal cylinder such as air cylinder and pneumatic cylinder. The reciprocal cylinder 45 has its cylinder main body 45a mounted and supported on the stand 50, and the front end of its piston rod 45b is connected to the lower side of the slide main body 44. Accordingly, when the piston rod 45b projects and invaginates, the slide main body 44 is moved reciprocally in the arrow direction between the wiping position D and wiping side changing position E described below.

The let-off reel 40 lets off the wound cleaning cloth T toward the cloth guide 42, and is rotatable about its support shaft 40a. The cleaning cloth T is in a tape form, and a non-fluffy water-absorbing fiber cloth of high fineness and high density is preferably used. Specifically, a synthetic fiber cloth of polyester and nylon is used as the cleaning cloth T. In the illustrated embodiment, one roll of cleaning cloth T of about 45 m is wound and stored in the let-off reel 40.

The take-up reel 41 is to take up the used cleaning cloth T through the cloth guide 42. The take-up reel 41 has its support shaft 41a driven and coupled by the rotary drive unit 43. The rotary drive unit 43 is specifically an electric motor such as servo motor, and is disposed upward in the lower surface of the slide main body 44 as shown in FIG. 6. The drive shaft 43a of this electric motor 43 is provided with a drive gear 51, and this drive gear x 51 is engaged with a follower gear 52 attached to the support shaft 41a. As a result, when the electric motor 43 is driven and rotates, the take-up reel 41 is rotated in the take up direction (arrow direction).

The cloth guide 42 guides and supports the cleaning cloth T let off from the let-off reel 40 so as to contact with the surface of the work W. The cloth guide 42 has a equilateral triangular shape in plan view, and its side faces 42A, 42B, 42C are support guide surfaces of the cleaning cloth T. The cloth guide 42 has its center or the position of the center of gravity rotatable freely about the support shaft 42a, between the both reels 40 and 41.

In this constitution, the cleaning cloth T let off from the let-off reel 40 is led into the cloth guide 42 through the guide roller 55 as shown in FIG. 5, and is guided along the support guide faces 42A, 42B, 42C. Afterwards, the cleaning cloth T is wound on the take-up reel 41 through the guide roller 56.

One of the support guide faces 42A, 42B, 42C of the cloth guide 42 (the support guide face 42B in the shown state) is located oppositely parallel to the work W chucked and supported in the work rotating device 2. At the confronting position, by the index rotation (arrow direction) of the cloth guide 42, one of the support guide faces 42A, 42B, 42C is sequentially positioned and stopped.

Figure 7:
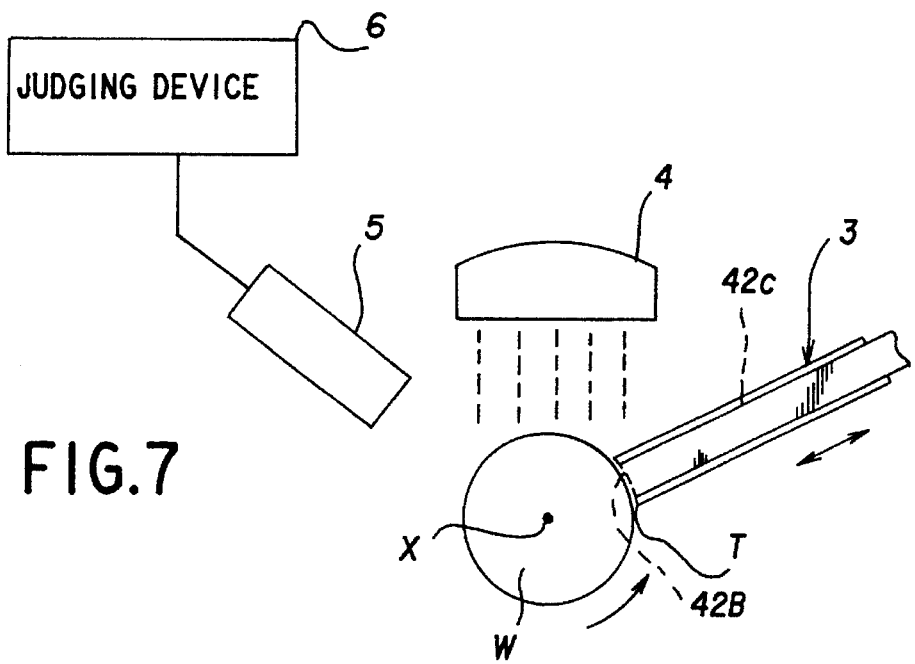
FIG. 7 is a schematic side view showing the configuration of the cleaning device, lighting device, line sensor camera and work in the surface flaw detecting apparatus.

For example, as shown in the drawing, the cleaning cloth T on the support guide face 42B positioned at the confronting position abuts against the surface of the work W chucked and supported by the work rotating device 2 at a specific pressure in the state of the slide main body 44 advanced to the cleaning position D (see FIGS. 5 to 7). In the abutting state of the cleaning cloth T, when the work W is rotated by the work rotating device 2, the surface soiling is wiped and removed over the entire length. Meanwhile, since the cloth guide 42 is rotatable freely about the support shaft 42a, the cleaning cloth T on the support guide face 42B contacts with the surface of the work W always stably and uniformly.

As the cleaning cloth T on the support guide face 42B wipes a plurality of works W, the wiping surface of the cloth (cleaning side) is gradually contaminated. When the cloth guide 42 rotates in index, and a next new support guide face 42C is used as the cleaning side. The index rotation at this time (cleaning side changing action) is conducted in cooperation with the winding action of the take-up reel 41 in the state of the slide main body 44 drawn back to the cleaning side changing position E.

That is, when the take-up reel 41 is rotated by the rotary drive unit 43 to take up the cleaning cloth T, the cloth guide 42 is rotated in index by ⅓ revolution in the arrow direction by the tensile force of the wound cleaning cloth T. As a result, the new cleaning side of the cleaning cloth T, that is, the cleaning side on the support guide face 42C is stopped at the confronting position to the work W (indexed).

Afterwards, the slide main body 44 is moved again forward to the cleaning position D, and the cleaning side on the support guide face 42C is brought into contact with the entire length of the surface of the work W chucked and supported in the work rotating device 2 (see FIG. 7).

The same action is repeated thereafter, and the cleaning side of the cleaning cloth T is always kept in a fresh state.

The index position of the cloth guide 42 is detected when a position sensor 100 attached to the slide main body 44 detects three detecting elements 101, 101, 101 attached to the cloth guide 42.

D. Lighting device 4

The lighting device 4 lights the surface of the work W chucked and supported by the work rotating device 2, and is arranged to light the work surface from top to bottom. As the lighting device 4, a fluorescent lamp or other linear lighting implement may be preferably used.

E. Line sensor camera 5

The line sensor camera 5 detects the reflected light from the surface of the work W illuminated by the lighting device 4, and specifically it detects the reflected light from the linear region in the axial direction on the work surface. The constitution of the line sensor camera 5 may be conventional and specific description of the constitution is omitted, and it generally comprises a lens having a same structure as an ordinary camera mechanism, a line sensor having a proper number of pixels, and a circuit for processing the detected signal of the line sensor, among others.

Figure 8:
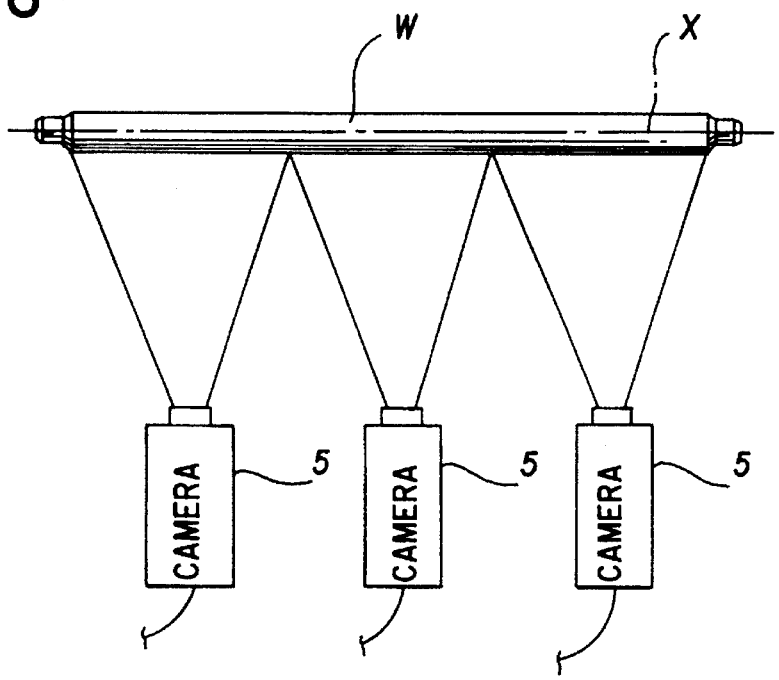
FIG. 8 is a schematic side view showing the configuration of the line sensor camera and work in the surface flaw detecting apparatus.

One or a plurality of line sensor cameras 5 are disposed on a stand 60 provided on the apparatus main body 25, depending on the axial length of the work W. In the illustrated embodiment, three line sensor cameras 5, 5, 5 are disposed parallel confronting the work W surface. That is, each line sensor camera 5 detects the surface of every ⅓ length of the work W as shown in FIG. 8.

These line sensor cameras 5, 5, 5 are configured as shown in FIG. 7, relatively to the cleaning device 3 and lighting device 4 (disposed at intervals of about 60 degrees in the rotating direction). Therefore, when the work W is rotated in the arrow direction by the work rotating device 2, the surface of the work W is designed to pass these confronting positions in the sequence of the cleaning device 3, lighting device 4, and line sensor cameras 5, 5, 5.

Theses line sensor cameras 5, 5, 5 read the state (reflected light) of the surface of works W while the work W makes one revolution by means of the work rotating device 2, and the result of detection is sent to the judging device 6. In the illustrated embodiment, more strictly, in relation also to the cleaning device 3, the surface state of the work W is read while the work W makes one and one third revolutions (⁴⁄₃ revolutions).

In the embodiment, the work W is rotated at a speed of about one revolution per second, and the reading speed by the line sensor camera 5 is also synchronized to read the surface state of the work W. Therefore, the reading time (measuring time) by work W is about 1 second.

As mentioned above, the lens of the line sensor camera 5 is same as an ordinary camera mechanism, and the surface state of the work W is imaged on the line sensor 5a (see FIG. 9).

For example, when a range of 100 mm in length on the surface of work W is imaged on the line sensor 5a with 5000 bits or 5000 pixels, the surface state of the work W is read at a resolution of 20 μm per bit.

When this line sensor 5a is driven by a 20 MHz drive clock 5b (see FIG. 9), the scanning speed is 250 sec, and therefore the surface state of the work W of 100 mm in length is read in 250 μsec.

Supposing the length of the work W to be 300 mm and the conditions of the line sensor camera 5 to be same as mentioned above, three line sensor cameras 5 are used as in the illustrated embodiment (see FIG. 8), and the scanning speed is 750 μsec.

Therefore, by rotating the work W at a speed of one revolution per second while synchronizing with the scanning speed of the line sensor 5a, the surface state of the work W of 20 mm in diameter and 300 mm in length is read at a surface resolution of 20 μm×20 μm. That is, the surface of the work W with the surface area of 18,840 mm² [=20 mm (diameter)×3.14 (ratio of the circumference of a circle to its diameter)×300 mm (length)] is read by resolving into 20 μm×20 μm=400 μm².

F. Judging device 6

The judging device 6 is to judge the presence or absence of flaw on the surface of the work W from the result of detection by the line sensor cameras 5, 5, 5, and comprises a signal processing unit and a judging unit, for example, as shown in FIG. 9.

The signal processing unit is to process electrically the detection signal (electric signal) from the line sensor camera 5. The signal processing unit comprises a band pass filter circuit 6a for removing the noise of the detected signal from the line sensor 5a, and a differentiating circuit 6b for detecting the amount of change of the detected signal being rid of noise. The judging unit comprises a judging circuit 6c, and the judging circuit 6c compares the processing value obtained in the signal processing unit (detected change amount level) with a predetermined value (reference electric signal level), and judges presence or absence of flaw of surface of the work W. The result judged by the judging circuit 6c is issued through an output circuit 6d.

G. Control device 7

The control device 7 is to drive and control electrically the constituent devices 1, 2, 3, 5 and 7 by synchronizing mutually, and is composed of microcomputer. The control device 7 is programmed to drive and control the constituent devices so as to rotate the work W about the axial line X, and detect surface flaw optically while removing soiling of the surface of the work W.

A specific flaw detecting process of the surface of the work W conducted according to the program is described below. In the following description, for the ease of understanding of the flaw detecting process, reference is made to one work W only.

i) The work W being conveyed by the inlet conveyor 20 is put into the work store 18 in the rotary loader device 1 at the work entry position A through the inlet chute 22.

ii) The work W put and held in the work store 18 is brought to the work chuck position B and stopped by the index rotation of the loader main body 10. The stopped work W is chucked (loaded) by the chuck devices 2a, 2b of the work rotating device 2.

iii) The work W chucked and held by the chuck devices 2a, 2b is rotated by a specified angle only in the arrow direction (in this embodiment, 4/3 revolutions as mentioned above) by rotary drive of the drive chuck unit 30. During revolution of the work W, specified optical measurement is done.

That is, the cleaning device 3 first advances to the cleaning position D, and wipes off soiling from the surface of the work W. The cleaned surface of the work W passes through the lighting device 4, and its reflected light is detected by the line sensor cameras 5, 5, 5. The result of detection is sent to the judging device 6, and presence or absence of flaw on the surface of the work W is judged.

iv) When specified optical measurement is completed, rotary drive of the drive chuck 30 is stopped, and the chucking support state of the work W by the chuck devices 2a, 2b is cleared. As a result, the measured work W is put and kept in the work store 18 waiting at the work chuck position B. In succession, the loader main body 10 is put in index rotation, and the work W is brought to the work exit position C and stopped, and is discharged on the outlet conveyor 21 through the outlet chute 23.

The work W discharged onto the outlet conveyor 21 is judged by the judging device 6, and when judged to be a flawless conforming piece, it is directly conveyed and recovered into a conforming piece recovering unit not shown by the outlet conveyor 21. If judged to be a defective piece having a flaw by the judging device 6, the work W is discharged into a defectives port 24 from the outlet conveyor 21 by means of defectives discharging device not shown.

v) Thereafter, the succeeding works W, W . . . are sequentially and continuously processed insteps i) to iv) above.

In thus constituted surface flaw detecting apparatus, the series of measuring and detecting operation is finished while the work W makes nearly one revolution about the axial line X by means of the work rotating device 2. Accordingly, in the surface flaw detecting apparatus of the invention, as compared with the conventional laser sensor system, the measuring time is shortened remarkably.

For example, in the embodiment, the work W rotates at a speed of about one revolution per second, and the reading speed of the line sensor camera 5 is synchronized therewith. Hence, the reading time (measuring time) by the line sensor camera 5 is about 1 second, and by adding the loading time by the rotary loader device 1, the line cycle time is about 6 seconds. As mentioned above, when measuring the work W of the same shape and size by three laser sensors a, a, a as shown in FIG. 9 (b), the measuring time is about 60 seconds, and the line cycle time is as long as about 80 seconds, and hence the time shortening effect of the apparatus of the invention is dramatic.

Moreover, using the line sensor camera 5, the mechanical motion during measuring in the apparatus is only rotation of the work W (and only about one revolution). Hence, there is almost no relative deflection between the work W and line sensor camera 5, and error in measurement is avoided, so that a high reliability is obtained in the measuring precision.

In the foregoing embodiment, the specific construction of the devices for constituting the surface flaw detecting apparatus is not limited to the illustrated examples alone, but may be appropriately modified as far as same functions are provided.

For example, the loader main body 10 which is a principal component for constituting the loader device 1 has a simple structure comprising a pair of index plates 13a, 13b in the shown example in consideration of reduction of cost and weight, etc., but the loader main body may be also formed in a cylindrical form and the work stores 18, 18, . . . may be provided on the outer circumference thereof.

The cloth guide 42 of the cleaning device 3 is a triangular shape in plan view which is the most compact polygonal shape in consideration of the space for installation and the like (see FIG. 5), but it may be formed in other polygonal shape such as quadrilateral and pentagonal shape, depending on the length of the work W and area of use of the cleaning cloth T.

The surface flaw detecting apparatus of the invention may be also applied in flaw detection and measurement of bar-shaped work having a tapered diameter, aside from bar-shaped work having same outside diameter over the enter length as shown in the embodiment.

As described herein, by the control means, while the work rotating means is rotating the work about the axial line, the cleaning means removes soiling from the work surface and the surface is illuminated by the lighting device, and the reflected light is detected by the sensor means, and the judging means judges presence or absence of flaw of work surface from the result of this detection, and therefore as compared with the flaw detecting apparatus by the laser sensor system above, the flaw detecting speed is fast, and the line cycle time can be shortened notably.

Figure 10A:
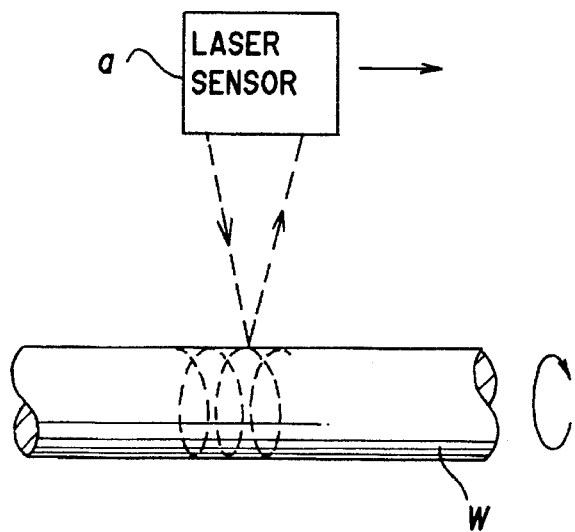
FIG. 10 is a schematic constitutional diagram showing a surface flaw detecting apparatus of workpiece similar to the invention for reference, showing a basic constitution in FIG. 10 (a) and its application constitution in FIG. 10 (b).
Figure 10B:
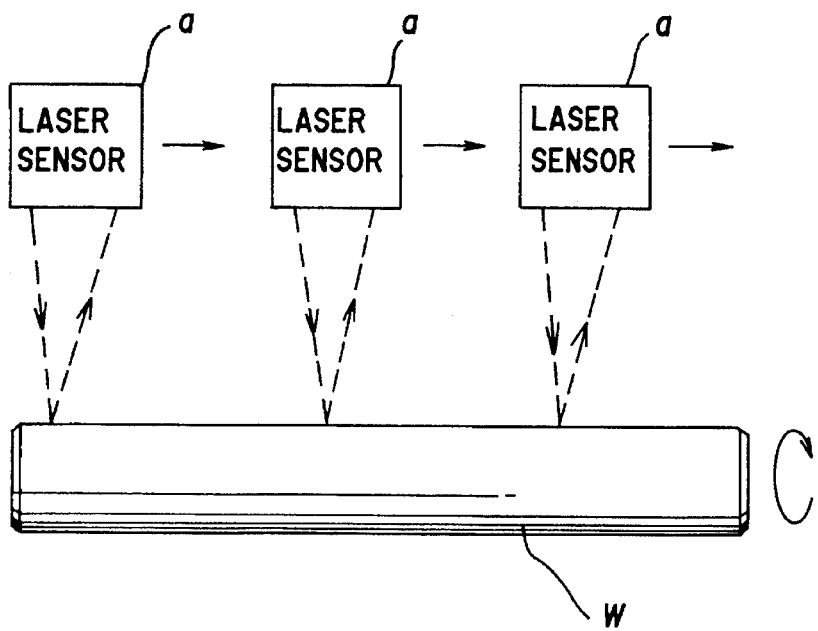

That is, in the laser sensor system, it is designed to scan spirally by moving the laser sensor in the axial direction of the work while rotating the work at high speed (see FIG. 10). In this apparatus, accordingly, the flaw detecting time per work is long, which is directly related with extension of line cycle time.

By contrast, in the flaw detecting apparatus of the invention, the flaw detecting operation is done while the work is nearly rotated a revolution by the work rotating means. Accordingly, as shown in the embodiment, the flaw detecting time per work in the apparatus is remarkably shortened as compared with that in the apparatus of the laser sensor system.

Still more, the work surface cleaning step which is done in a separate step in principle is done automatically by the cleaning means in cooperation with the rotary motion of the work, and therefore this process time has almost no effect on the line cycle time.

Moreover, when the work loading and unloading on the work rotating means is designed to be done by the loader means which makes index rotation, the time required for loading is shortened, and the line cycle time can be further shortened.

In the apparatus of the invention, further, by employing the line sensor means, mechanical motion during flaw detecting measurement is only the rotation of the work, and this rotating range is set in a small range of about one revolution, and therefore relative deflection between the work and sensor means hardly occurs, and occurrence of measuring error may be avoided. As a result, in the apparatus of the invention, as compared with the laser sensor system, it is expected to obtain a high reliability and high precision in measurement.

In the apparatus of the invention, mechanical moving parts are fewer than in the laser sensor system, and the entire construction may be simple and compact, and the apparatus cost may be kept low.

What is more, the apparatus of the invention is low in the trouble incidence and is expected to lower the running cost. Incidentally, as compared with the laser sensor system having a similar measuring precision, it has been verified that the apparatus of the invention is realized at the cost of about 60%.

As the invention may be embodied in several forms without departing from the spirit of essential characteristics thereof, the present embodiments are therefore illustrative and not restrictive, since the scope of the invention is defined by the appended claims rather than by the description preceding them, and all changes that fall within metes and bounds of the claims, or equivalence of such metes and bounds thereof are therefore intended to be embraced by the claims.

What is claimed is:

1. A surface flaw detecting apparatus of workpiece comprising:

work rotating means for rotating a workpiece about its axial line, cleaning means for removing soiling from the surface of workpiece, lighting means for illuminating the surface of workpiece, line sensor means for detecting reflected light from the surface of workpiece, judging means for judging presence or absence of flaw on the surface of workpiece from the detection result of the line sensor means, and control means for driving and controlling these constituent means by synchronizing mutually, wherein the control means is designed to drive and control each constituent means so as to rotate the workpiece about its axial line, and detect the surface flaw optically while removing soiling from the surface of workpiece.

2. A surface flaw detecting apparatus of workpiece of claim 1, wherein the individual means are disposed so that the flaw detecting position on the surface of workpiece may pass in the sequence of the cleaning means, lighting means and line sensor means, by rotation of the workpiece by the work rotating means.

3. A surface flaw detecting apparatus of workpiece of claim 1, wherein the work rotating means comprises first and second chuck means, being disposed at both ends of the workpiece in the axial direction, so as to rotate the workpiece while chucking and supporting its ends, the first chuck means comprises a drive chuck unit for chucking one end of the workpiece, and a rotary drive unit for rotating the drive chuck unit, and the second chuck means comprises a follower chuck unit for rotatably chucking and supporting the other end of the workpiece.

4. A surface flaw detecting apparatus of workpiece of claim 3, further comprising:

loader means for loading and unloading the workpiece on the work rotating means, the loader means is in a form of a rotary loader device disposed between the first and second chuck means of the work rotating means, the rotary loader device comprises a loader main body rotatably supported about an axial line parallel to the work rotary axial line of both chuck devices, and a rotary drive unit for rotating the loader main body by index, and work stores for supporting the workpieces in a state parallel to the work rotary axial line of the both chuck devices are disposed at plural positions at equal intervals in the peripheral direction, on the outer circumference of the loader main body.

5. A surface flaw detecting apparatus of workpiece of claim 4, wherein the index rotary locus of the work stores is set at a position not interfering with the chucks in the moving range of the chucks of the both chuck means, and the configuration of the work stores is defined so that two of them may be indexed at the work entry position and work exit position while the other one is indexed at the work chuck position.

6. A surface flaw detecting apparatus of workpiece of claim 5, wherein inlet conveyor means, both the chuck means, and outlet conveyor means are respectively disposed at the work entry position, work chuck position, and work exit position, corresponding to the configuration of the work stores of the loader main body.

7. A surface flaw detecting apparatus of workpiece of claim 5, wherein the work stores of the loader main body are formed in pockets opened to the outer circumference of the loader main body, exchange of workpiece between the work stores and the both conveyors is effected as the workpiece rolls and drops by its own weight between the two, and exchange of workpiece between the work stores and the chuck means is effected as the workpiece is lifted or lowered to the work stores by the chucking motion of the chuck means.

8. A surface flaw detecting apparatus of workpiece of claim 1, wherein the cleaning means comprises a let-off reel on which a tape of cleaning cloth is wound, a take-up reel for taking up and recovering the used cleaning cloth, a cloth guide disposed between these two reels for guiding and supporting the cleaning cloth let off from the let-off reel so as to be in contact with the surface of workpiece, and rotary drive means for rotating in take up direction the take-up reel.

9. A surface flaw detecting apparatus of workpiece of claim 8, wherein the cloth guide of the cleaning means is nearly triangular in its plane shape, each side face is used as the support guide face of the cleaning cloth, and the position of its center of gravity is rotatably supported, and the cloth guide is rotated in index in cooperation with the rotary motion of the take-up reel by the rotary driving means, so that the cleaning surface position of the cleaning cloth confronting the workpiece is varied.

10. A surface flaw detecting apparatus of workpiece of claim 9, wherein the cleaning device comprises a slide main body supporting the take-up reel, let-off reel, cloth guide and drive unit, being reciprocally movable between the cleaning position and cleaning side changing position, and a reciprocal drive unit for moving the slide main body reciprocally between the forward position and backward position, and the cleaning cloth of the cloth guide abuts against the surface of workpiece at the forward position of the slide main body, and the index rotation of the cloth guide is allowed at the backward position of the slide main body.

11. A surface flaw detecting apparatus of workpiece of claim 9, wherein the index rotation of the cloth guide is effected by the tensile force of the cleaning cloth caused at the time of rotary motion of the take-up reel by the rotary drive means.

12. A surface flaw detecting apparatus of workpiece of claim 8, wherein the cleaning cloth of the cleaning means is made of non-fluffy water-absorbing fiber cloth high in fineness and high in density.

13. A surface flaw detecting apparatus of workpiece of claim 1, wherein the lighting means is a linear lighting implement such as fluorescent lamp.

14. A surface flaw detecting apparatus of workpiece of claim 1, wherein the sensor means is composed of line sensor cameras for detecting reflected light from the linear region in the axial direction on the surface of workpiece, and one or a plurality of line sensor cameras are disposed parallel to the surface of workpiece, depending on the axial length of the workpiece.

15. A surface flaw detecting apparatus of workpiece of claim 1, wherein judging means comprises a signal processing unit for processing the detection signal from the sensor means electrically, and a judging unit for comparing the processed value obtained in the signal processing unit with a predetermined value, and judging presence or absence of flaw on the surface of workpiece.

* * * * *